United States Patent
Cho

(10) Patent No.: US 9,925,322 B2
(45) Date of Patent: *Mar. 27, 2018

(54) DIALYSATE SUPPLY DEVICE AND BLOOD DIALYZING APPARATUS HAVING THE SAME

(71) Applicant: Taebeom Cho, Daejeon (KR)

(72) Inventor: Taebeom Cho, Daejeon (KR)

(73) Assignee: HUMAN BIOMED, INC.

( * ) Notice: Subject to any disclaimer, the term of this patent is extended or adjusted under 35 U.S.C. 154(b) by 0 days.

This patent is subject to a terminal disclaimer.

(21) Appl. No.: 15/301,709

(22) PCT Filed: Mar. 31, 2015

(86) PCT No.: PCT/KR2015/003223
§ 371 (c)(1),
(2) Date: Oct. 3, 2016

(87) PCT Pub. No.: WO2015/152623
PCT Pub. Date: Oct. 8, 2015

(65) Prior Publication Data
US 2017/0095604 A1   Apr. 6, 2017

Related U.S. Application Data

(63) Continuation-in-part of application No. 14/243,943, filed on Apr. 3, 2014, now Pat. No. 9,682,182.

(30) Foreign Application Priority Data

Jul. 10, 2014 (KR) .......................... 10-2014-0087127
Nov. 25, 2014 (KR) .......................... 10-2014-0164876
Nov. 25, 2014 (KR) .......................... 10-2014-0164967

(51) Int. Cl.
*A61M 1/26* (2006.01)
*A61M 1/16* (2006.01)
(Continued)

(52) U.S. Cl.
CPC .......... *A61M 1/267* (2014.02); *A61M 1/1643* (2014.02); *A61M 1/1649* (2014.02);
(Continued)

(58) Field of Classification Search
None
See application file for complete search history.

(56) References Cited

U.S. PATENT DOCUMENTS 4,935,125 A     6/1990  Era et al.
5,466,228 A *  11/1995  Evans ................. F16K 11/0853
                                                              137/625.47
(Continued)

FOREIGN PATENT DOCUMENTS

JP    2004-041742      2/2004
JP    P2012-165891     9/2012
(Continued)

OTHER PUBLICATIONS

International Search Report (PCT/KR2015/003223, dated Jul. 28, 2015).
(Continued)

*Primary Examiner* — Krishnan S Menon
(74) *Attorney, Agent, or Firm* — Lee & Associates, LLC

(57) ABSTRACT

Provided is a dialysate supply device and a blood dialyzing apparatus including the same. The dialysate supply device includes a flow controller controlling a dialysate flow, a supply pump supplying dialysate to a hemodialyzer, a recovery pump discharging dialysate from the hemodialyzer, a volume chamber storing dialysate, and a pressure-relief bypass maintaining dialysate pressure within a permissible range. The blood dialyzing apparatus includes the dialysate supply device, a blood tube, and a one-way valve disposed on the blood tube. The blood dialyzing apparatus can quickly change dialysate pressure in the hemodialyzer using (Continued)

the dialysate supply device having the flow controller, cylinder and piston, and increase mass transfer and hemodialysis efficiency. Also, the blood dialyzing apparatus may be miniaturized and lightened to provide a portable blood dialyzing apparatus because blood is transferred without using a blood pump.

16 Claims, 12 Drawing Sheets

(51) Int. Cl.
| | |
|---|---|
| *B01D 61/28* | (2006.01) |
| *B01D 61/32* | (2006.01) |
| *B01D 61/30* | (2006.01) |
| *F04B 23/06* | (2006.01) |
| *F04B 1/02* | (2006.01) |
| *F04B 43/12* | (2006.01) |
| *F04B 19/20* | (2006.01) |
| *F04B 43/08* | (2006.01) |
| *F04B 51/00* | (2006.01) |
| *F04B 43/02* | (2006.01) |
| *F04B 49/24* | (2006.01) |
| *A61M 39/24* | (2006.01) |

(52) U.S. Cl.
CPC ........... *A61M 1/1668* (2014.02); *B01D 61/28* (2013.01); *B01D 61/30* (2013.01); *B01D 61/32* (2013.01); *F04B 1/02* (2013.01); *F04B 19/20* (2013.01); *F04B 23/06* (2013.01); *F04B 43/02* (2013.01); *F04B 43/08* (2013.01); *F04B 43/1253* (2013.01); *F04B 49/24* (2013.01); *F04B 51/00* (2013.01); *A61M 39/24* (2013.01); *A61M 2205/3334* (2013.01); *A61M 2205/3337* (2013.01); *A61M 2205/3341* (2013.01); *A61M 2205/3365* (2013.01); *B01D 2313/19* (2013.01)

(56) References Cited

U.S. PATENT DOCUMENTS 8,870,804 B2 * 10/2014 Jonsson ................. A61M 1/16
  604/4.01
9,168,332 B2 * 10/2015 Wada ..................... A61M 1/16

FOREIGN PATENT DOCUMENTS

| | | |
|---|---|---|
| JP | P5205036 | 2/2013 |
| KR | 10-2004-0026193 | 3/2004 |
| KR | 10-2011-0088438 | 8/2011 |
| KR | 10-2011-0096707 | 8/2011 |
| KR | 10-2013-0124039 | 11/2013 |
| KR | 10-2014-0068343 | 6/2014 |

OTHER PUBLICATIONS

Written Opinion of International Search Authority for PCT/KR2015/003223.

* cited by examiner

FIG. 2A
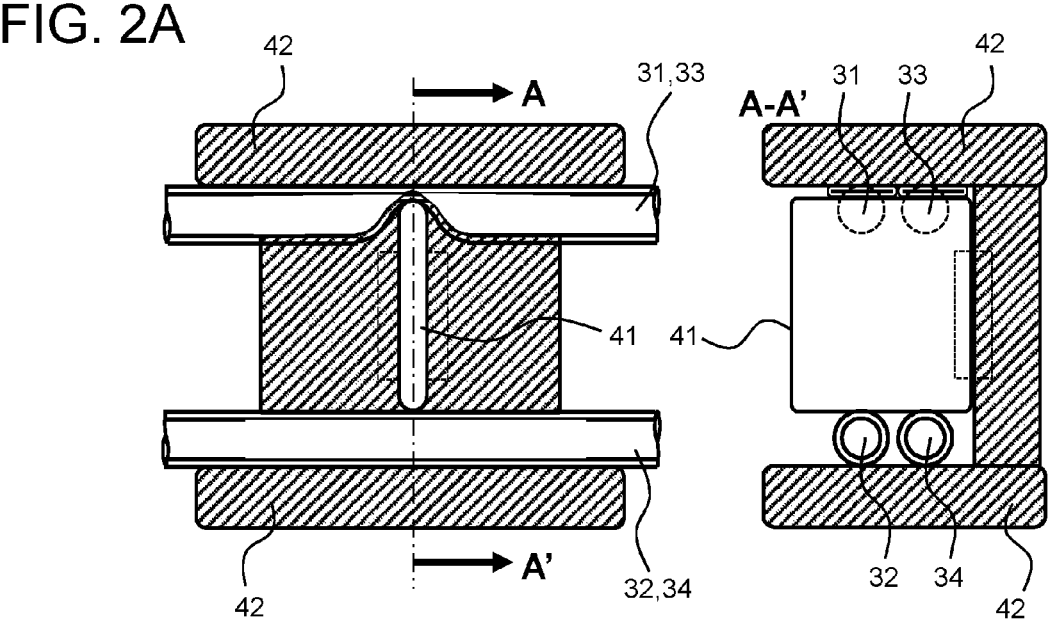
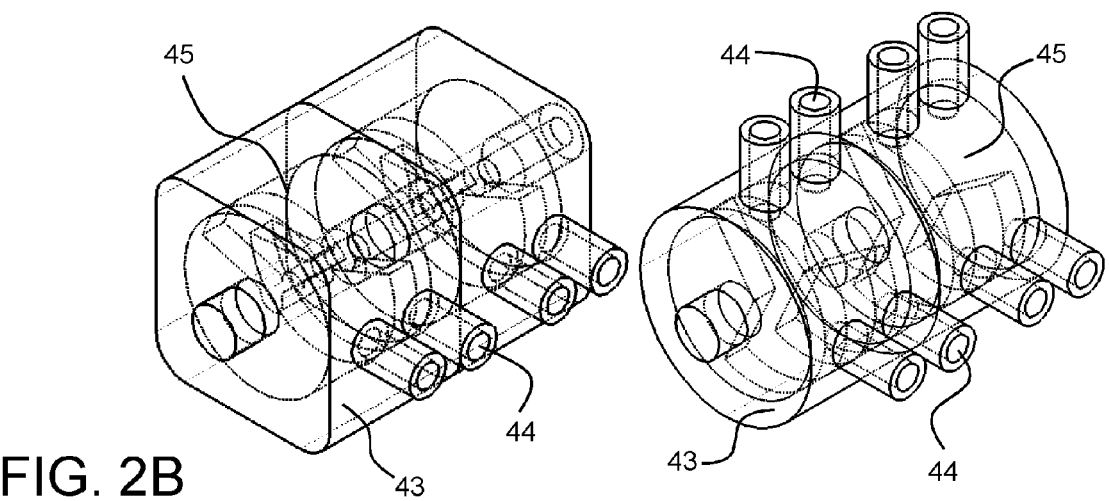
FIG. 2B

DIALYSATE SUPPLY DEVICE AND BLOOD DIALYZING APPARATUS HAVING THE SAME

CROSS-REFERENCE TO RELATED APPLICATIONS

This application is a national stage application of International Patent Application No. PCT/KR2015/003223 filed on Mar. 31, 2015, which claims priority to U.S. patent application Ser. No. 14/243,943 filed on Apr. 3, 2014, Korean Patent Application No. 10-2014-0087127 filed on Jul. 10, 2014, Korean Patent Application No. 10-2014-0164967 filed on Nov. 25, 2014, and Korean Patent Application No. 10-2014-0164876 filed on Nov. 25, 2014, the entire contents of which are incorporated by reference herein.

TECHNICAL FIELD

The present invention generally relates to a hemodialysis to remove impurities in blood by circulating blood and dialysate, and more particularly, to a dialysate supply device and a blood dialyzing apparatus including the dialysate supply device which is configured to improve water exchange and mass transfer between blood and dialysate by quickly changing the dialysate pressure in a hemodialyzer using a pulsatile dialysate flow.

BACKGROUND

When there is a kidney dysfunction, water and waste products that have to be discharged out of body accumulate in blood and imbalance of electrolytes in the body occurs. Most commonly performed to improve such a kidney failure symptom, is hemodialysis which is to circulate blood out of body and rid the blood of the accumulated uremic toxin and excess water by a semi-permeable dialysis membrane. Hemodialysis is a method of seeking an electrolyte balance and ridding the body fluid of uremic toxin and excess water, taking advantages of diffusion applied due to the concentration difference and filtration applied due to the pressure difference between blood and dialysate, while circulating blood through a side of the semi-permeable membrane and dialysate through the other side thereof.

A hemodialyzer having a structure where semi-permeable membrane is disposed in a single container is used such that mass transfer between blood and dialysate easily occurs. Most commonly used of the hemodialyzer is the hollow-fiber membrane type that is a cylinder-shape container charged with a semi-permeable membranes and port-processed at opposite ends thereof by use of a synthetic resin like polyurethane.

Blood and dialysate each decrease their hydraulic pressure while passing through a hemodialyzer. Since blood and dialysate flow in opposite directions inside the hemodialyzer, filtration occurs at the proximal part of the hemodialyzer such that water in the blood moves toward dialysate compartment because blood pressure is higher than dialysate pressure, while backfiltration occurs at the distal part such that water in the dialysate moves toward blood domain for the same reason.

When water in the blood moves toward the dialysate compartment, wastes in blood are also eliminated, which is referred to as a convective mass transfer. It is known that uremic toxins of medium molecular size are efficiently removed by the convective mass transfer and thus dialysis efficiency and prognosis on patients have greatly improved. However, there is a big hurdle in the effort to improve dialysis efficiency by the convective mass transfer, because hemodialyzers in typical hemodialysis apparatuses are limited in size and blood flow rate is restrictively allowed to be increased in consideration of the weight and blood vessel condition of a patient.

SUMMARY OF THE DISCLOSURE

The present invention provides a dialysate supply device and a blood dialyzing apparatus including the dialysate supply device which can improve hemodialysis efficiency by regulating a pressure difference between blood and dialysate without increasing the size of a hemodialyzer or the flow rate of blood.

Embodiments of the present invention provide a dialysate supply device which includes a dialysate tube in which dialysate flows, a supply pump supplying dialysate to a hemodialyzer, a recovery pump discharging dialysate from the hemodialyzer, and a flow controller controlling a dialysate flow through the dialysate tube.

The dialysate tube may include a first dialysate tube to supply dialysate to the supply pump, a second dialysate tube to supply dialysate of the supply pump to the hemodialyzer, a third dialysate tube to discharge dialysate of the hemodialyzer to the recovery pump, and a fourth dialysate tube to discard dialysate of the recovery pump. The flow controller may open or block a dialysate flow through the first to fourth dialysate tube. Specifically, when two dialysate tubes among the four dialysate tubes are blocked by the flow controller, other two dialysate tubes may be opened.

To this end, the flow controller may include a flow-blocking member reciprocating in a straight line, a flow-blocking member driver for driving the flow-blocking member, and a support wall supporting the dialysate tube. Alternatively, the flow controller may include a housing, a flow port disposed on an outer surface of the housing, a rotor disposed inside the housing and tightly attached into the inner surface of the housing to connect a flow passage between flow ports.

The supply pump and the recovery pump may include a cylinder having an internal space, a piston disposed inside the cylinder to compress or expand the cylinder, and a piston driver allowing the piston to reciprocate. Here, the cylinder of the supply pump and the cylinder of the recover pump may be simultaneously compressed or expanded. The cylinder and piston may be changed into a sac formed of a flexible material that can contract and expand and a sac pressurizing member which can compress and expand the sac. Similarly, the sac pressurizing member compresses or expands the sac of the supply pump and the sac of the recovery pump at the same time. Also, the supply pump and the recovery pump according to an embodiment of the present invention may include a roller compressing the dialysate tube to transfer dialysate therein, a roller driver driving the roller, and a reservoir storing dialysate.

Further, the dialysate supply device according to the present invention may include a volume chamber that is connected to the third dialysate tube to store dialysate.

Regarding the operation of the dialysate supply device, when the cylinders of the supply pump and the recovery pump are expanded, the flow controller opens the first and third dialysate tubes and blocks the second and fourth dialysate tubes. Due to the expansion of the cylinder of the supply pump, dialysate of the supply tank flows into the cylinder. Due to the expansion of the cylinder of the recovery pump, dialysate of the hemodialyzer flows into the cylinder. When the dialysate of the hemodialyzer flows into the cylinder of the recovery pump, since the second dialysate tube is blocked, the hydraulic pressure of dialysate in the hemodialyzer is lowered compared to the hydraulic pressure of blood, and thus filtration occurs.

On the other hand, when the cylinder of the supply pump and the cylinder of the recovery pump are compressed, the flow controller blocks the first and third dialysate tubes and opens the second and fourth dialysate tubes. Due to the compression of the cylinder of the recovery pump, the dialysate of the cylinder is discharged. Due to the compression of the cylinder of the supply pump, the dialysate of the cylinder is supplied to the hemodialyzer. When dialysate is supplied to the hemodialyzer, since the third dialysate tube is blocked, the hydraulic pressure of dialysate in the hemodialyzer increases compared to the hydraulic pressure of blood, and thus backfiltration occurs. Thus, when the cylinders are expanded, a TMP of the hemodialyzer has a positive (+) value and filtration occurs. On the contrary, when the cylinders are compressed, the TMP becomes a negative (−) value and backfiltration occurs. The TMP can be defined as a pressure difference between the blood pressure and dialysate passing through the hemodialyzer.

As described above, the dialysate pressure decreases when the cylinders are expanded whereas it increases when the cylinders are compressed. When the dialysate pressure fluctuates, the dialysate supply device according to an embodiment of the present invention may further include a pressure-relief bypass which connects between the third dialysate tube and the fourth dialysate tube, allowing the dialysate pressure to be maintained in a permissible range. In addition, the dialysate supply device according to an embodiment of the present invention may additionally include a method to measure the amount of dialysate supplied to the hemodialyzer and the amount of dialysate collected from the hemodialyzer.

The blood dialyzing apparatus according to an embodiment of the present invention includes the aforementioned dialysate supply device, the hemodialyzer in which mass transfer occurs between blood and dialysate, a blood tube connecting a patient and the hemodialyzer, and a blood pump disposed on the blood tube to transfer blood. Also, the blood dialyzing apparatus may additionally have an auxiliary dialysate tube connecting the third dialysate tube and the fourth dialysate tube and an auxiliary dialysate pump disposed on the auxiliary dialysate tube to additionally remove dialysate from the hemodialyzer. In this case, the blood pump may be replaced with a one-way valve disposed on the blood tube to allow blood to flow in a predetermined direction. The blood tube may include a first blood tube to supply blood to the hemodialyzer and a second blood tube to return blood of the hemodialyzer to a patient.

When the filtration occurs by the operation of the dialysate supply device, blood of a patient is supplied to the hemodialyzer through the first blood tube due to the one-way valve disposed on the blood tube. On the other hand, when there is backfiltration in the hemodialyzer, blood of the hemodialyzer is returned to a patient through the second blood tube.

The dialysate supply device according to an embodiment of the present invention can quickly change the dialysate pressure inside the hemodialyzer using the flow controller and the supply and recovery pumps including the cylinder and the piston. As a result, water exchange and mass transfer between blood and dialysate inside the hemodialyzer can be increased upon hemodialysis, thereby improving hemodialysis efficiency without increasing the size of the hemodialyzer or the flow rate of blood and dialysate. In addition, since blood is transferred without using a blood pump, the blood dialyzing apparatus may be further miniaturized and lightened.

BRIEF DESCRIPTION OF DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIGS. 2A and 2B are views illustrating a flow controller;

DETAILED DESCRIPTION OF PREFERRED EMBODIMENTS

Figure 1:
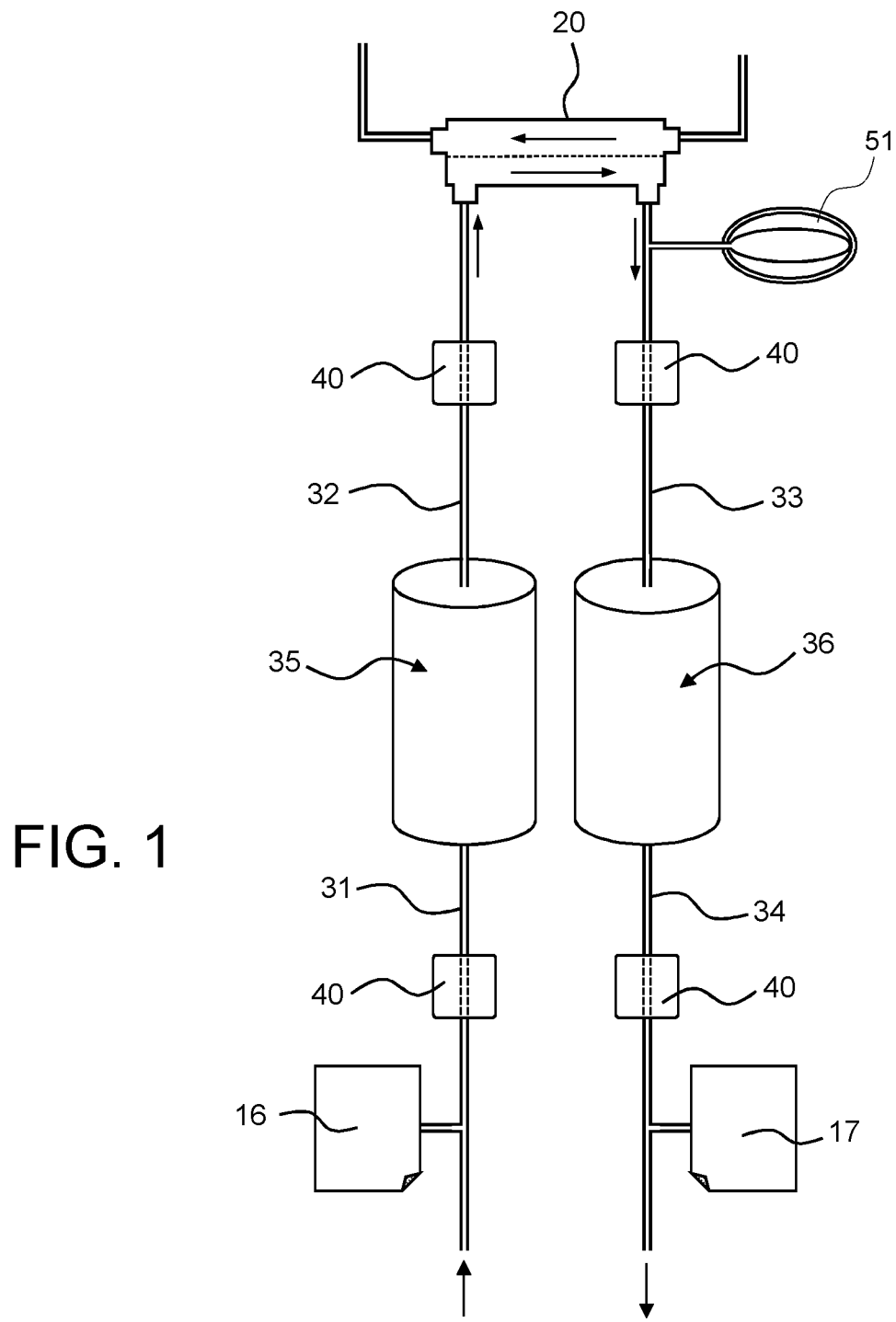
FIG. 1 is a schematic view illustrating a dialysate supply device according to an embodiment of the present invention.

Hereinafter, a dialysate supply device and a blood dialyzing apparatus having the dialysate supply device according to an embodiment of the present invention will be described in detail with reference to the accompanying drawings.

In the following description of the present invention, the size, shape or the like of constituent elements illustrated in the drawings may be exaggerated or simplified for clarity and convenience of explanation. Also, the terms particularly defined taking into consideration the configurations and operations of the present invention may be changed based on the intentions of users or operators, or customs. These terms should be construed as meanings and concepts conforming to the technical spirit of the present invention based on the general context of this specification.

As illustrated in FIG. 1, the dialysate supply device 30 according to an embodiment of the present invention may include dialysate tubes 31 to 34 in which dialysate flows, a supply pump 35 supplying dialysate to a hemodialyzer 20, a recovery pump 36 discharging dialysate having passed through the hemodialyzer, and a flow controller 40 controlling a flow through the dialysate tubes.

Dialysate may be used in a form of a dialysate bag that is previously made or manufactured by adjusting pH and electrolyte concentration in the ultrapure water prepared through a water treatment system. The manufactured dialysate may be supplied to the hemodialyzer 20 through the supply pump 35 and the dialysate having passed through the hemodialyzer 20 may be discharged by the recovery pump 36. The dialysate tube may include a first dialysate tube 31 to supply dialysate to the supply pump, a second dialysate tube 32 to supply dialysate of the supply pump to the hemodialyzer, a third dialysate tube 33 to discharge dialysate of the hemodialyzer 20 to the recovery pump, and a fourth dialysate tube 34 to discard dialysate of the recovery pump. Also, the dialysate supply device 30 according to an embodiment of the present invention may further include a supply tank 16 storing dialysate and a recovery tank 17 collecting used dialysate. For example, the fresh dialysate can be stored in the supply tank 16 and then supplied to the hemodialyzer 20, and used dialysate having passed the hemodialyzer may be collected into the recovery tank 17. However, the dialysate can be supplied directly to the hemodialyzer 20 without being stored in the supply tank and the used dialysate can be directly discarded without being collected in the recover tank, thereby inhibiting contamination of dialysate.

The flow controller 40 may open or block a dialysate flow through the first to fourth dialysate tube 31 to 34. Specifically, when two dialysate tubes among the four dialysate tubes are opened by the flow controller 40, other two dialysate tubes may be blocked. For example, when the first and third dialysate tubes 31 and 33 are blocked, the second and fourth dialysate tubes 32 and 34 are opened. Similarly, when the first and third dialysate tubes 31 and 33 are opened, the second and fourth dialysate tubes 32 and 34 are blocked.

As shown in FIG. 2A, in order to open or block the dialysate tubes, the flow controller 40 may include a flow-blocking member 41 reciprocating in a straight line, a flow-blocking member driver for driving the flow-blocking member, and a support wall 42 supporting the dialysate tube. For example, when the flow-blocking member 41 compresses the first and third dialysate tubes 31 and 33 to block flow therethrough, the second and fourth dialysate tubes 32 and 34 are opened. In contrast, when the flow-blocking member 41 blocks the second and fourth dialysate tubes 32 and 34, the first and third dialysate tubes 31 and 33 may be opened.

The flow-blocking member driver may include various structures that can apply a reciprocating movement force to the flow-blocking member 41. An exemplary flow-blocking member driver may include a cam for pushing the flow-blocking member 41 toward the support wall 42 supporting the dialysate tube and a motor for rotating the cam. When the flow-blocking member 41 compresses the dialysate tube due to the rotation of the cam, the flow passage therethrough may be blocked. When an external force by the cam is removed, the flow-blocking member 41 may detach from the dialysate tube, and the dialysate tube may be restored to the original state by its own elastic force, expanding the inside of the tube. Or, an eccentric cam connected to a motor may rotate and compress one side of the tube, and thus block the flow passage through the compressed tube. The cam further rotates such that an external force applied by the cam may be removed and the tube is restored to its original status, expanding the inside of the tube.

Alternatively, the flow controller 40 may include a housing 43, a flow port 44 disposed on an outer surface of the housing, a rotor 45 disposed inside the housing and tightly attached into the inner surface of the housing 51 to connect a flow passage between flow ports 44, as illustrated in FIG. 2B. Due to the rotation of the rotor 45, when a flow passage is connected between two flow ports, the flow passage through other flow ports that are not connected may be desirably blocked. The time for opening or blocking the flow passage may be controlled by regulating the rotation speed of the rotor 45.

As shown in FIG. 2A, the flow-blocking member 41 of the flow controller 40 according to an embodiment of the present invention may open or block two dialysate tubes at the same time. Similarly, in the case of the flow controller 40 which includes the housing 43 and the rotor 45, two dialysate tubes can be simultaneously opened or blocked by the rotor. However, the flow controller according to an embodiment of the present invention is not limited to the structure shown in the drawings. In order to regulate the dialysate flow, the flow controller 40 may be provided separately in the tubes 31 and 32 through which dialysate is supplied to the hemodialyzer and in the tubes 33 and 34 through which dialysate of the hemodialyzer is discharged. Thus, the flow controller 40 according to an embodiment of the present invention may be modified into various structures that can alternately open and block the first and third dialysate tubes, and the second and fourth dialysate tubes.

Figure 3:
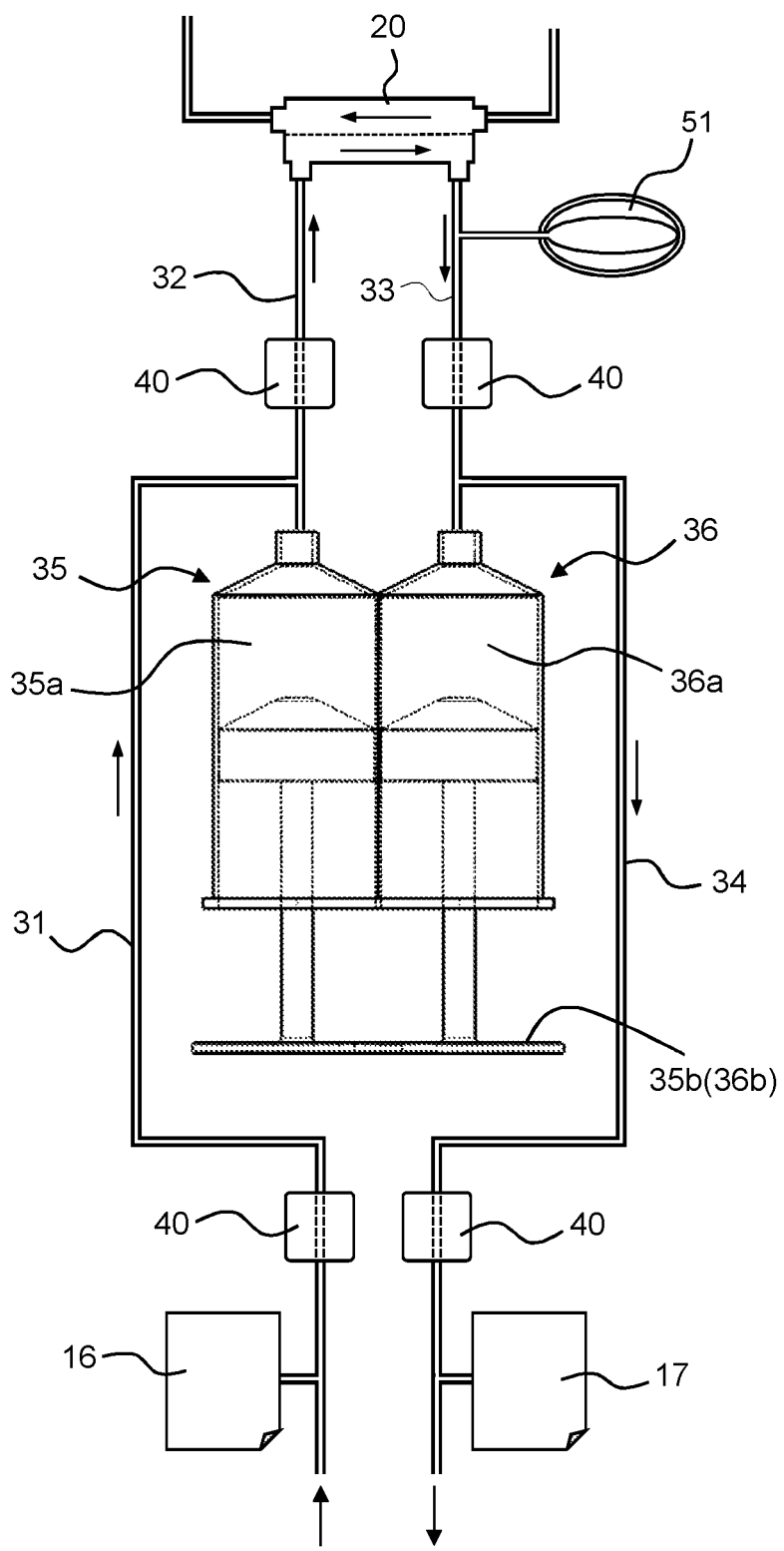
FIGS. 3 to 5 are views illustrating a dialysate supply device according to an embodiment of the present invention.

The supply pump 35 and the recovery pump 36 may include various structures that can transfer dialysate. As shown in FIG. 3, the supply pump 35 and the recovery pump 36 may include a cylinder 35a and 36a having an internal space, a piston 35b and 36b disposed inside the cylinder to compress or expand the cylinder, and a piston driver allowing the piston to reciprocate. The piston driver may include various structures that can compress or expand the cylinder by pushing or pulling the piston. Here, the cylinder 35a of the supply pump and the cylinder 36a of the recover pump may be simultaneously compressed or expanded.

Figure 4:
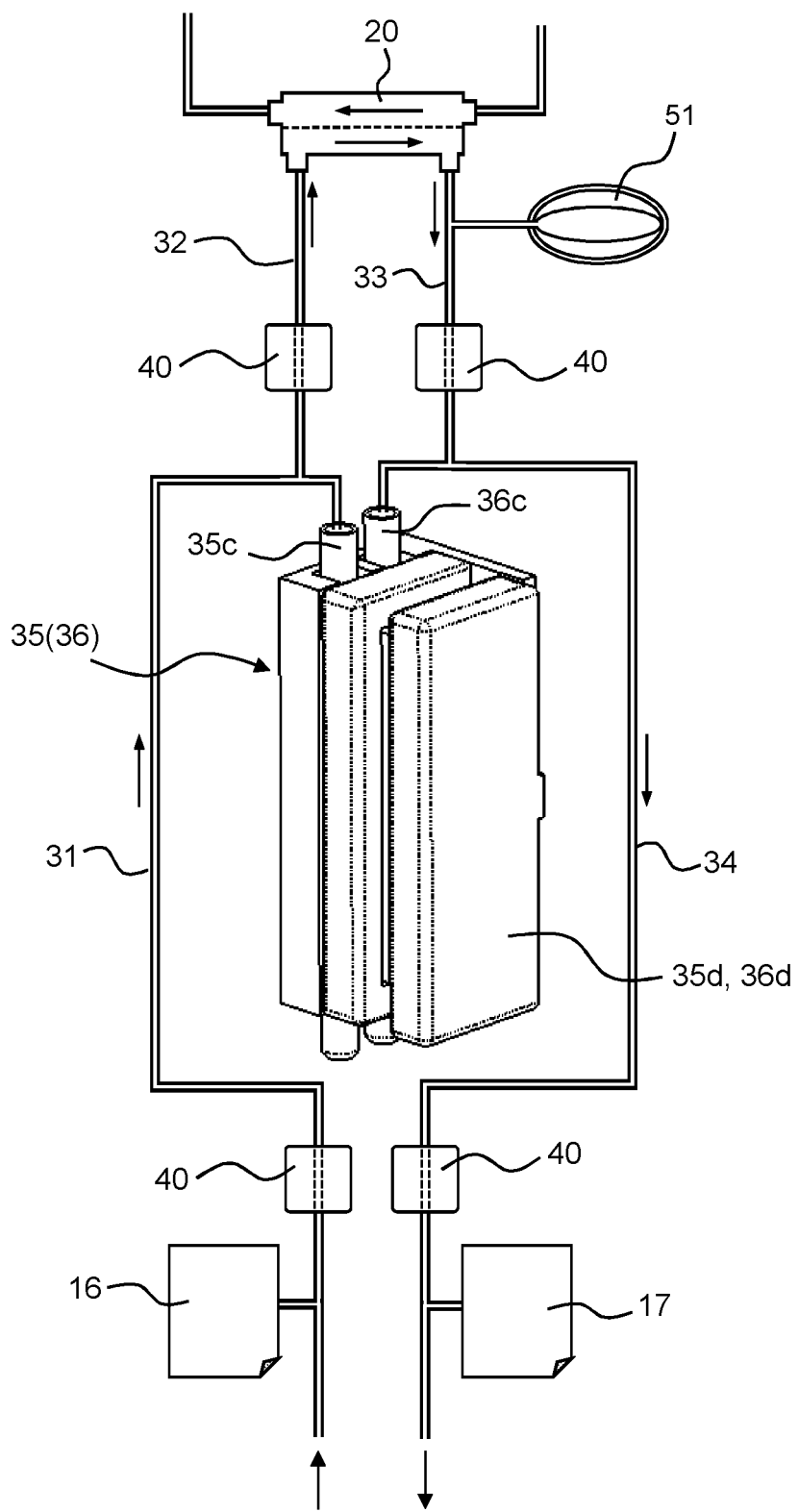

When dialysate is transferred by the compression and expansion of the cylinder by the piston, the cylinder and piston may be modified into a sac 35c and 36c formed of a flexible material that can contract and expand and a sac pressurizing member 35d and 36d which can compress and expand the sac, respectively. FIG. 4 illustrates the dialysate supply device 30 having supply and recovery pumps 35 and 36 which include the sac and sac pressurizing member. The sac pressurizing member compresses or expands the sac 35c of the supply pump and the sac 36c of the recovery pump at the same time while rectilinearly moving along a guide rail disposed on one side wall. The sac pressurizing member driver may be modified to have another structure that can apply a reciprocating movement force to the sac pressurizing member.

Figure 5:
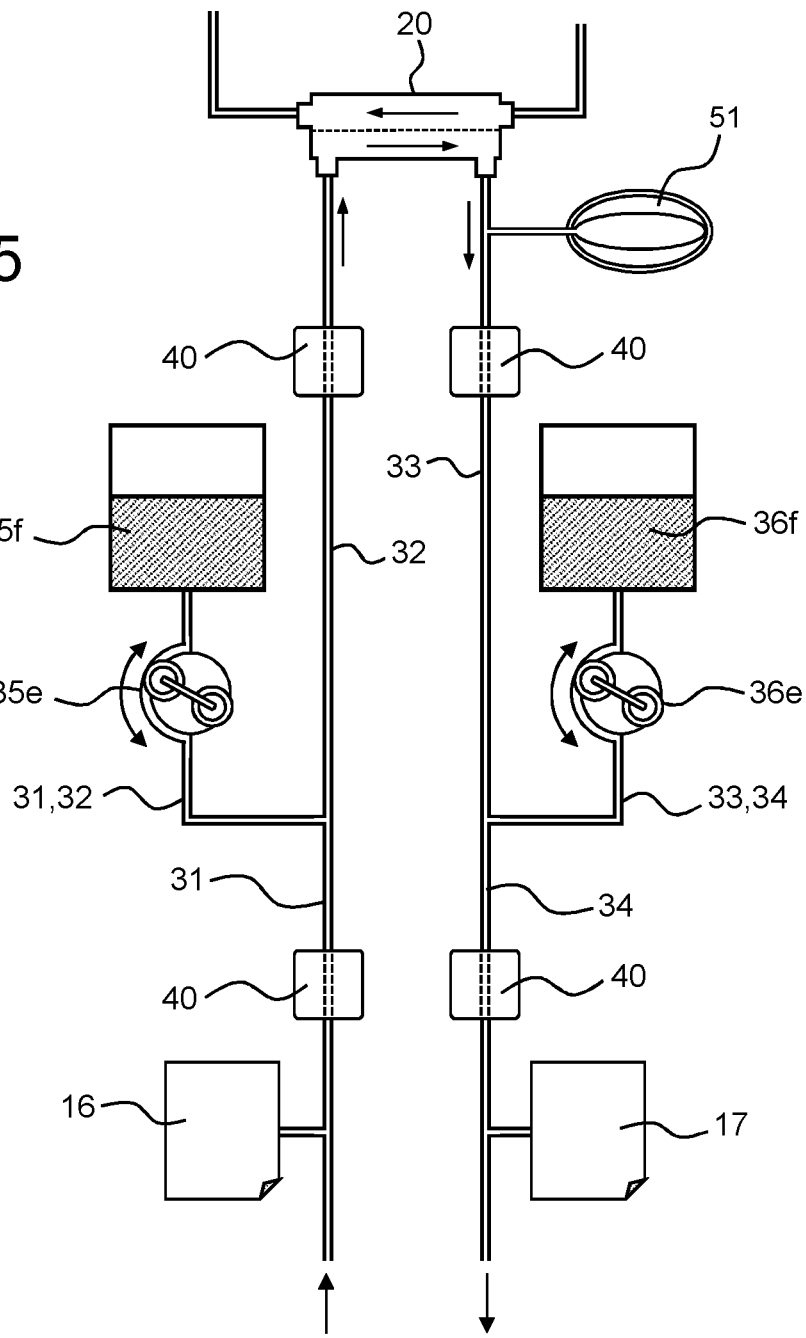

Also, as shown in FIG. 5, the supply pump 35 and the recovery pump 36 according to an embodiment of the present invention may include a roller 35e and 36e compressing the dialysate tube to transfer dialysate therein, a roller driver driving the roller, and a reservoir 35f and 36f storing dialysate. When dialysate is transferred by rotation of the roller, the roller driver may use various methods that rotate the roller. The roller is not limited to transfer dialysate by its rotational movement, but the roller and roller driver may be modified into other structures to transfer dialysate, including, but not limited to, a rectilinear movement of the roller or sequential compression of the dialysate tube by a plurality of rollers. The rollers 35e and 36e of the supply pump and the recovery pump rotate or rectilinearly move in a same direction, and accordingly the supply pump and the recovery pump may be operated by a single roller and roller driver.

The reservoirs 35f and 36f stores dialysate. The exemplary reservoir includes a fluid bag formed of a flexible material that expands when dialysate flows in and contracts when the dialysate flows out. Also, a container made of a hard material may be used for the reservoir, such that the pressure inside the reservoir increases when dialysate flows in and decreases when dialysate flows out. The reservoirs may be modified into various structures that can store or discharge dialysate.

In addition, as illustrated in FIGS. 3 to 5, the dialysate supply device 30 according to the present invention may further include a volume chamber 51 that is connected to the third dialysate tube 33 to store dialysate. FIGS. 3 and 5 illustrate the volume chamber comprising a container having an internal space and a fluid sac disposed inside the container that can contract and expand. The fluid sac expands or contracts when dialysate flows into or out of the container. The fluid sac has a maximum volume of dialysate due to the container surrounding the fluid sac. The volume chamber 51 is not limited to the structure shown in the drawings, and may be modified into other structures to accommodate or discharge dialysate. The volume chamber may also be modified to be connected to the second dialysate tube 32.

Hereinafter, an operation of the dialysate supply device 30 according to an embodiment of the present invention will be described in detail with reference to the accompanying drawings.

Figures 6A, 6B:
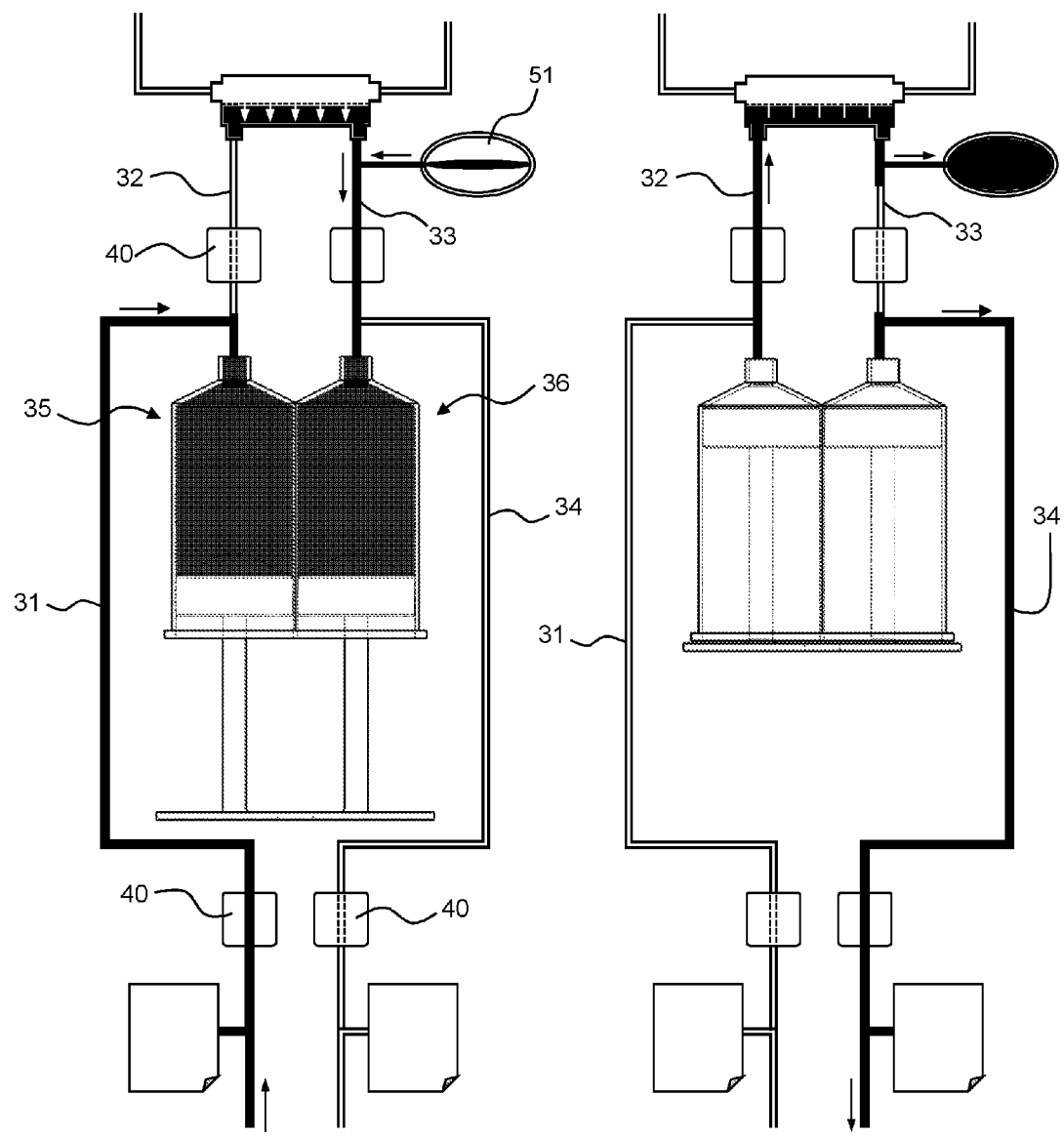
FIGS. 6A, 6B, 7A and 7B are views illustrating an operation of a dialysate supply device according to an embodiment of the present invention.

As shown in FIG. 6A, when the cylinder 35a of the supply pump and the cylinder 36a of the recovery pump are expanded, the flow controller 40 opens the first and third dialysate tubes 31 and 33 and blocks the second and fourth dialysate tubes 32 and 34. Due to the expansion of the cylinder 35a of the supply pump, dialysate of the supply tank 16 flows into the cylinder 35a. Due to the expansion of the cylinder 36a of the recovery pump, dialysate of the hemodialyzer 20 flows into the cylinder 36a. In this case, dialysate stored in the volume chamber 51 may be discharged toward the cylinder 36a of the recovery pump. When the dialysate of the hemodialyzer flows into the cylinder 36a of the recovery pump, since the second dialysate tube 32 is blocked, the hydraulic pressure of dialysate in the hemodialyzer is lowered compared to the hydraulic pressure of blood, and thus filtration in which water and waste products in blood move to the dialysate flow region occurs.

On the other hand, as shown in FIG. 6B, when the cylinder 35a of the supply pump and the cylinder 36a of the recovery pump are compressed, the flow controller 40 blocks the first and third dialysate tubes 31 and 33 and opens the second and fourth dialysate tubes 32 and 34. Due to the compression of the cylinder 36a of the recovery pump, the dialysate of the cylinder is discharged toward the recovery tank 17 or discarded therefrom. Due to the compression of the cylinder 35a of the supply pump, the dialysate of the cylinder is supplied to the hemodialyzer 20. In this case, a portion of dialysate having passed through the hemodialyzer 20 may be stored in the volume chamber 51. When dialysate is supplied to the hemodialyzer, since the third dialysate tube 33 is blocked, the hydraulic pressure of dialysate in the hemodialyzer increases compared to the hydraulic pressure of blood, and thus backfiltration in which water in the dialysate moves toward the blood flow region occurs. The dialysate tubes illustrated with solid black in the drawings represent that there is a dialysate flow therethrough.

When the cylinders 35a and 36a are expanded, a TMP of the hemodialyzer 20 has a positive (+) value and filtration occurs. On the contrary, when the cylinders are compressed, the TMP becomes a negative (−) value and backfiltration occurs. The TMP can be defined as a pressure difference between the blood pressure and dialysate passing through the hemodialyzer 20. Thus, a cycle of expansion and compression of the supply pump 35 and the recovery pump 36 configures a cycle of filtration and backfiltration, and in the hemodialysis using the dialysate supply device 30 according to an embodiment of the present invention, the cycle of filtration and backfiltration is repeated, removing water and waste products during filtration and supplementing lost water during backfiltration.

Figures 7A, 7B:
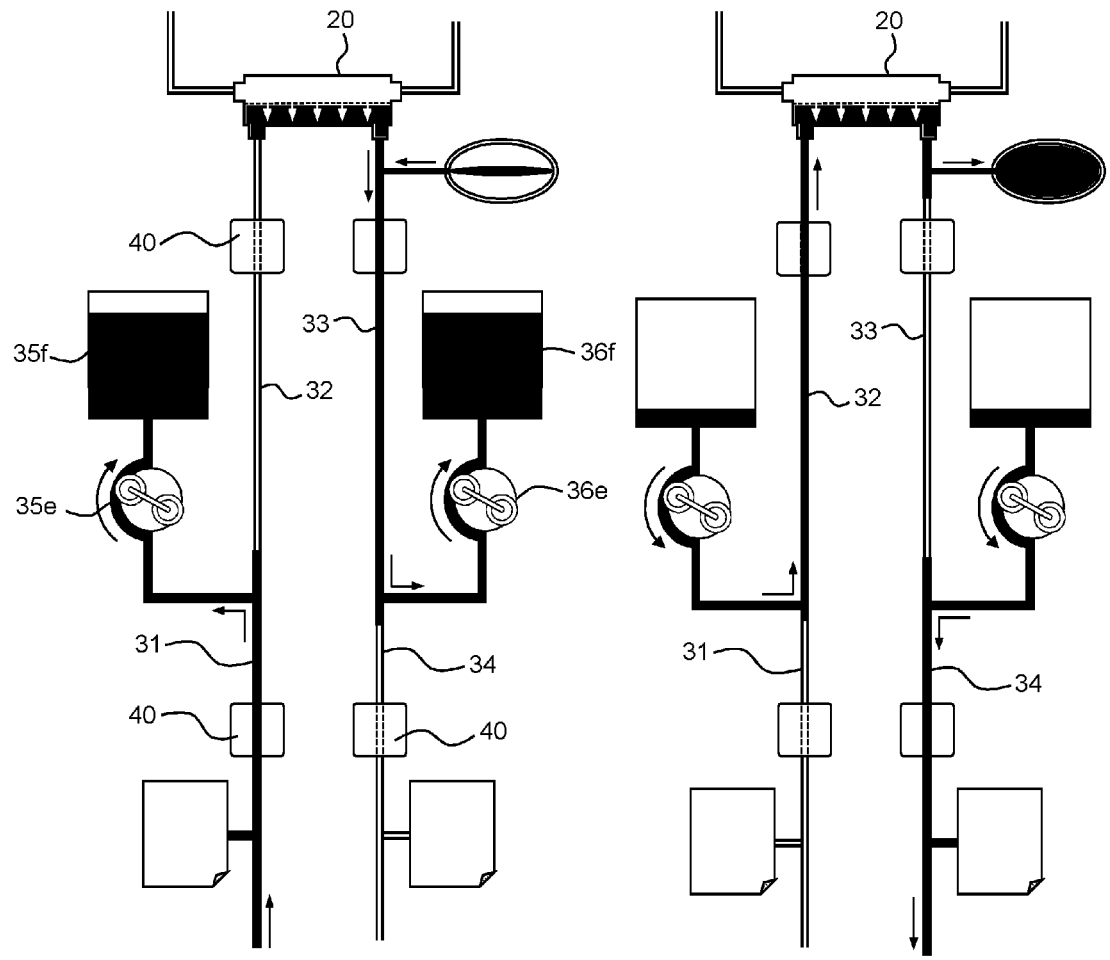

FIGS. 7A and 7B illustrate an operation of the dialysate supply device 30 comprising the roller 35e and 36e and the reservoir 35f and 36f. As shown in FIG. 7A, the roller 35e of the supply pump and the roller 36e of the recovery pump rotate in a direction (a clockwise direction in the drawing), the flow controller 40 opens the first and third dialysate tubes 31 and 33 and blocks the second and fourth dialysate tubes 32 and 34. Dialysate is supplied to the reservoir 35f of the supply pump by the rotation of the roller 35e of the supply pump and dialysate of the hemodialyzer flows into the reservoir 36f of the recovery pump by the rotation of the roller 36e of the recovery pump. In this case, the dialysate of the volume chamber 51 may flow into the reservoir 36f of the recovery pump. When the dialysate of the hemodialyzer flows into the reservoir 36f of the recovery pump, since the second dialysate tube 32 is blocked, the dialysate pressure of the hemodialyzer is lowered compared to the blood pressure, resulting in the filtration in which water and waste products in blood move to the dialysate flow region.

On the other hand, as shown in FIG. 7B, the roller 35e of the supply pump and the roller 36e of the recovery pump rotate in a reverse direction (a counterclockwise direction in the drawing), the flow controller 40 blocks the first and third dialysate tubes 31 and 33 and opens the second and fourth dialysate tubes 32 and 34. Dialysate of the reservoir 36f of the recovery pump is discharged therefrom by the roller 36e of the recovery pump, and dialysate of the reservoir 35f of the supply pump is supplied to the hemodialyzer 20 by the roller 35e of the supply pump. In this case, a portion of dialysate having passed through the hemodialyzer 20 may be stored in the volume chamber 51. When the dialysate of the reservoir 35f of the supply pump is supplied to the hemodialyzer, since the third dialysate tube 33 is blocked, the dialysate pressure of the hemodialyzer increases compared to the blood pressure and backfiltration in which water in the dialysate moves to the blood flow region occurs.

When the rollers 35e and 36e rotate in a direction, the TMP of the hemodialyzer 20 becomes a positive (+) value and the filtration occurs. On the contrary, when the rollers 35e and 36e rotate in a reverse direction, the TMP becomes a negative (−) value and the backfiltration occurs. Thus, a cycle of rotation and reverse rotation of the rollers of the supply pump 35 and the recovery pump 36 configures a cycle of filtration and backfiltration.

Here, the volume rate of filtration (QUF, ml/stroke) and backfiltration (QBF) may be calculated. The dialysate tubes 32 and 33 may have a fixed volume without being contracted or expanded despite the change in the pressure therein. The QUF and QBF may be expressed by an Equation (1) using a compression-expansion volume of the cylinder 36a of the recovery pump (Ve), a compression-expansion volume of the cylinder 35a of the supply pump (Vd), and a volume of the volume chamber 51 (Vc).

$$QUF = Ve - Vc, QBF = Vd - Vc \qquad (1)$$

Here, in the case of the dialysate supply device 30 comprising the sac and sac pressurizing member, Vd and Ve may be the volumes of compression and expansion of the sacs, and for the dialysate supply device 30 comprising the roller and reservoir, Vd and Ve may represent the volumes of dialysate to be stored in the reservoir and to be discharged from the reservoir, respectively.

Also, the number of compression and expansion per minute (cycle/minute) of the cylinder, or the number of rotation and reverse rotation of the roller may be appropriately controlled according to the prescription of dialysate flow rate that is required for the hemodialysis treatment. For example, in the hemodialysis treatment, assuming that blood and dialysate are prescribed to flow at the rate of 250 and 600 ml/min, respectively, and if the internal compression-expansion volume (Veda and Vet) of the cylinders 35$a$ and 36$a$ is 20 ml, the supply pump 35 and the recovery pump 36 need 30 compression-expansion cycles per minute. According to the Equation (1), the QUF and QBF may be controlled by the volume (Vc) of the volume chamber 51.

Here, the dialysate can be transferred by the compression and expansion of the cylinder 35$a$ and 36$a$ by the piston 35$b$ and 36$b$, the compression and expansion of the sac 35$c$ and 36$c$ by the sac pressurizing member 35$d$ and 36$d$, or the rotation and reverse rotation of the roller 35$e$ and 36$e$ in substantially the same way, such that the dialysate pressure is regulated and the filtration and backfiltration occur. As such, hereinafter, the dialysate supply device 30 having the cylinder and piston will be principally described, which may be applied to the dialysate supply device including the sac and sac pressurizing member, or the dialysate supply device including the roller and reservoir in the same way.

Figures 8A, 8B:
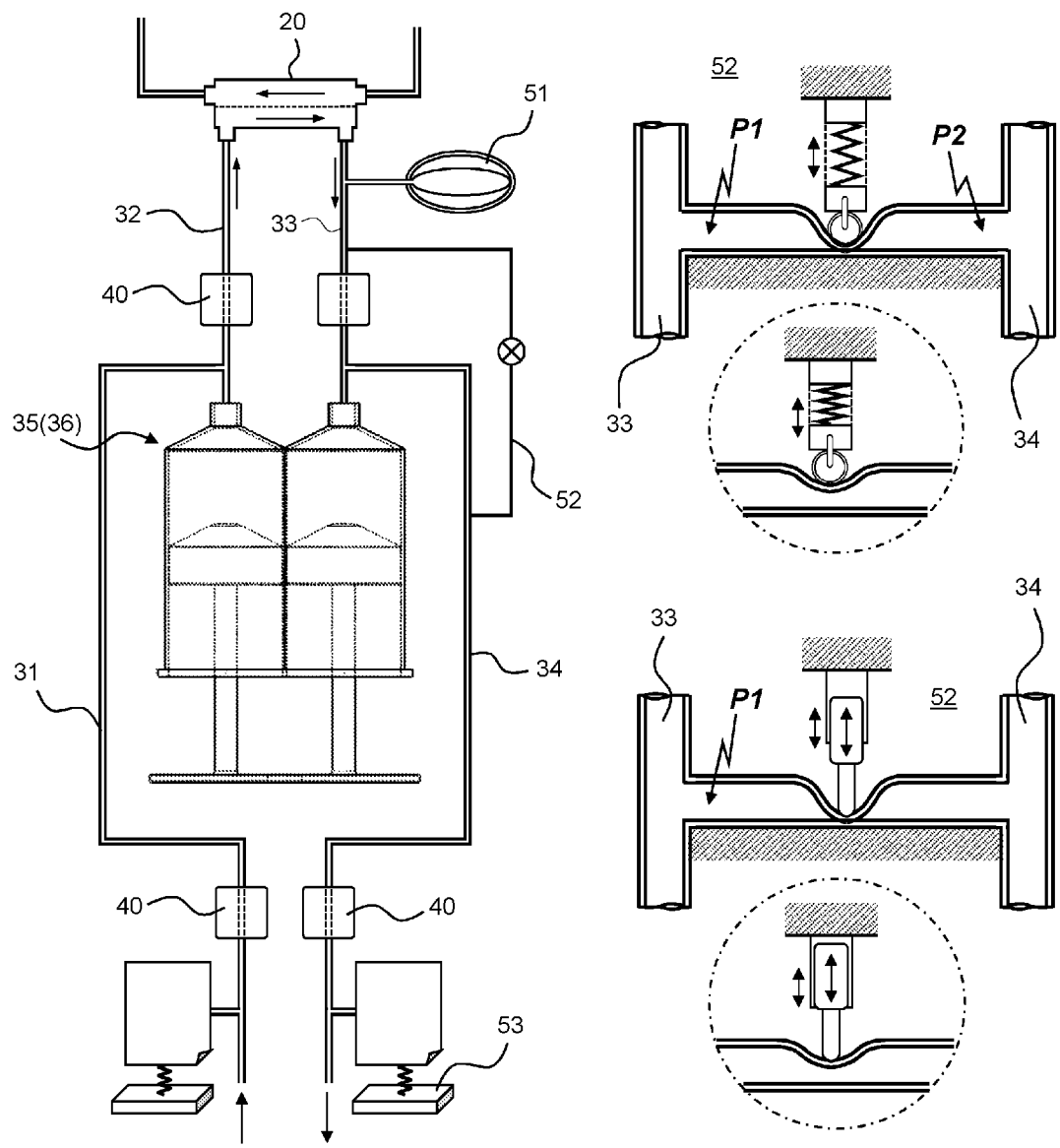
FIGS. 8A and 8B are views illustrating a dialysate supply device having a balance and a pressure relief bypass, respectively.

As described above, the dialysate pressure decreases when the cylinders 35$a$ and 36$a$ are expanded whereas it increases when the cylinders are compressed. When the dialysate pressure fluctuates, the dialysate supply device 30 according to an embodiment of the present invention may further include a pressure-relief bypass 52 which connects between the third dialysate tube 33 and the fourth dialysate tube 34, allowing the dialysate pressure to be maintained in a permissible range. FIG. 8A illustrates the dialysate supply device 30 having the pressure-relief bypass 52. Since the fourth dialysate tube 34 may be connected to the recovery tank 17, an end of the pressure-relief bypass 52 may be directly connected to the recovery tank 17.

When the pressure of the third dialysate tube 33, i.e., the dialysate pressure inside the hemodialyzer 20, increases above the permissible range, the dialysate of the hemodialyzer may be discharged to the recovery tank 17 through the pressure-relief bypass 52. On the contrary, when the dialysate pressure decreases below the permissible range, dialysate of the recovery tank may be supplemented to the hemodialyzer through the pressure-relief bypass 52. An exemplary pressure-relief bypass is illustrated in FIG. 8B. Under the normal operation, the pressure-relief bypass remains closed due to the compression of the spring. However, when the dialysate pressure (P1) of the third dialysate tube 33 exceeds the spring compression, the spring moves upwardly in the drawing and the pressure-relief bypass opens. The pressure-relief bypass 52 is not limited to be opened or closed by the pressure of the third dialysate tube. Rather, the pressure-relief bypass can be opened or closed by the pressure of the second dialysate tube 32, the pressure difference (P1−P2) of the both tubes connected by the pressure-relief bypass 52, or the transmembrane pressure (TMP) of the hemodialyzer 20.

The pressure value that can open or close the pressure-relief bypass 52 is not limited to have a predetermined value, but may be dependent on the membrane of the hemodialyzer. In general, the hemodialyzer membrane has a limit of the TMP, e.g., a positive (+) value limit and a negative (−) value limit. Although the TMP limits depend on the kind of membrane that is used, it may approximately have an absolute value of 300 to 2,500 mmHg. When the pressure of the third dialysate tube decreases (approximately a pressure value between −300 and −2,500 mmHg), the dialysate of the recovery tank may be supplemented to the third dialysate tube through the pressure-relief bypass. In contrast, when the pressure of the third dialysate tube increases (approximately a pressure value between 300 and 2,500 mmHg), the dialysate of the third dialysate tube may be removed to the recovery tank 17 through the pressure-relief bypass 52. Thus, the pressure of dialysate flowing through the hemodialyzer can be maintained in the permissible range due to the pressure-relief bypass 52. The pressure-relief bypass 52 is not limited to connect between the third dialysate tube 33 and the fourth dialysate tube 34, but may be modified to connect between the first dialysate tube 31 and the second dialysate tube 32, which operation is substantially identical to that of the pressure-relief bypass 52 illustrated in FIG. 8A.

In addition, the dialysate supply device 30 according to an embodiment of the present invention may additionally include a method to measure the amount of dialysate supplied to the hemodialyzer and the amount of dialysate collected from the hemodialyzer 20. For example, as shown in FIG. 8A, a balance 53 of the supply tank and the recovery tank may be provided to measure the amount of dialysate supplied from the supply tank 16 and collected in the recovery tank 17 during hemodialysis. Since water is not easily removed from the body of a patient with renal failure, it is important to remove excess water from the body upon hemodialysis. The amount of water that is removed from a patient during hemodialysis can be determined using the difference in the amount of dialysate that was supplied to and collected from the hemodialyzer. The method of measuring the amount of dialysate supplied to the hemodialyzer and the amount of dialysate collected from the hemodialyzer is not limited to the balance 53 shown in the drawing. The amount of water removed from a patient can be measured by a flowmeter provided on the dialysate tubes 31 and 32 through which dialysate is supplied to the hemodialyzer and by a flowmeter provided on the dialysate tubes 33 and 34 through which dialysate is collected from the hemodialyzer. Alternatively, in the case of the dialysate supply device 30 having the roller and reservoir, the weight of the reservoirs 35$f$ and 36$f$ or pressure inside the reservoirs may provide the information on the amount of dialysate supplied or discharged.

Hereinafter, the blood dialyzing apparatus 10 according to an embodiment of the present invention will be described in detail with reference to the accompanying drawings.

Figure 9:
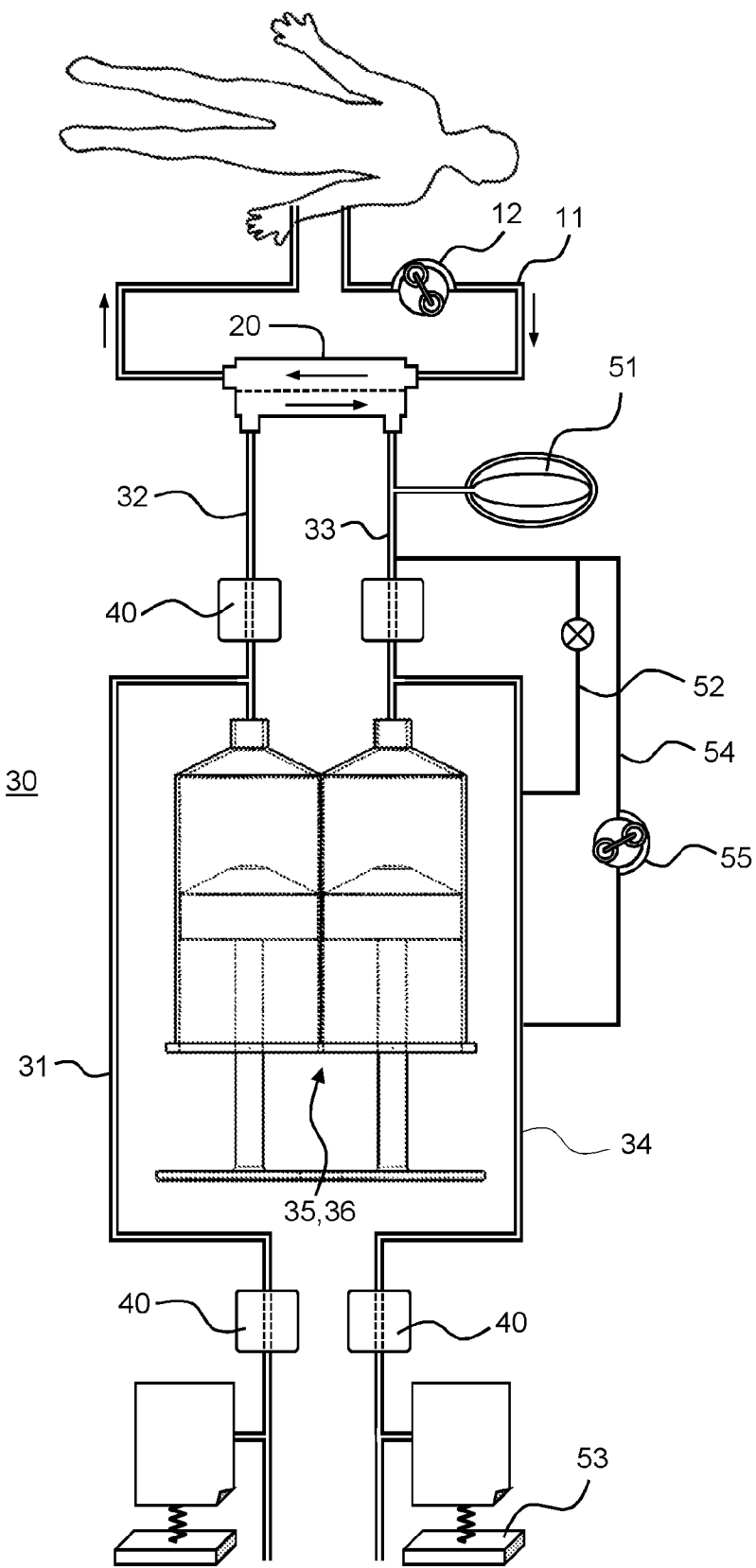
FIG. 9 is a schematic view illustrating a blood dialyzing apparatus including a blood pump according to an embodiment of the present invention.

As shown in FIG. 9, the blood dialyzing apparatus 10 according to an embodiment of the present invention includes the aforementioned dialysate supply device 30, the hemodialyzer 20 in which mass transfer occurs between blood and dialysate, a blood tube 11 connecting a patient and the hemodialyzer 20, and a blood pump 12 disposed on the blood tube to transfer blood. A roller pump that transfers blood by squeezing a blood tube is illustrated as the blood pump in the drawing, but the blood pump is not limited to the roller pump and may be modified into various ways to transfer blood.

Also, the blood dialyzing apparatus 10 according to an embodiment of the present invention may additionally have an auxiliary dialysate tube connecting the third dialysate tube 33 and the fourth dialysate tube 34 and an auxiliary dialysate pump disposed on the auxiliary dialysate tube to additionally remove dialysate from the hemodialyzer. When the dialysate flows by the operation of the supply pump 35 and the recovery pump 36, water (e.g., dialysate) may be additionally removed from the hemodialyzer by the operation of the auxiliary dialysate pump.

Figure 10:
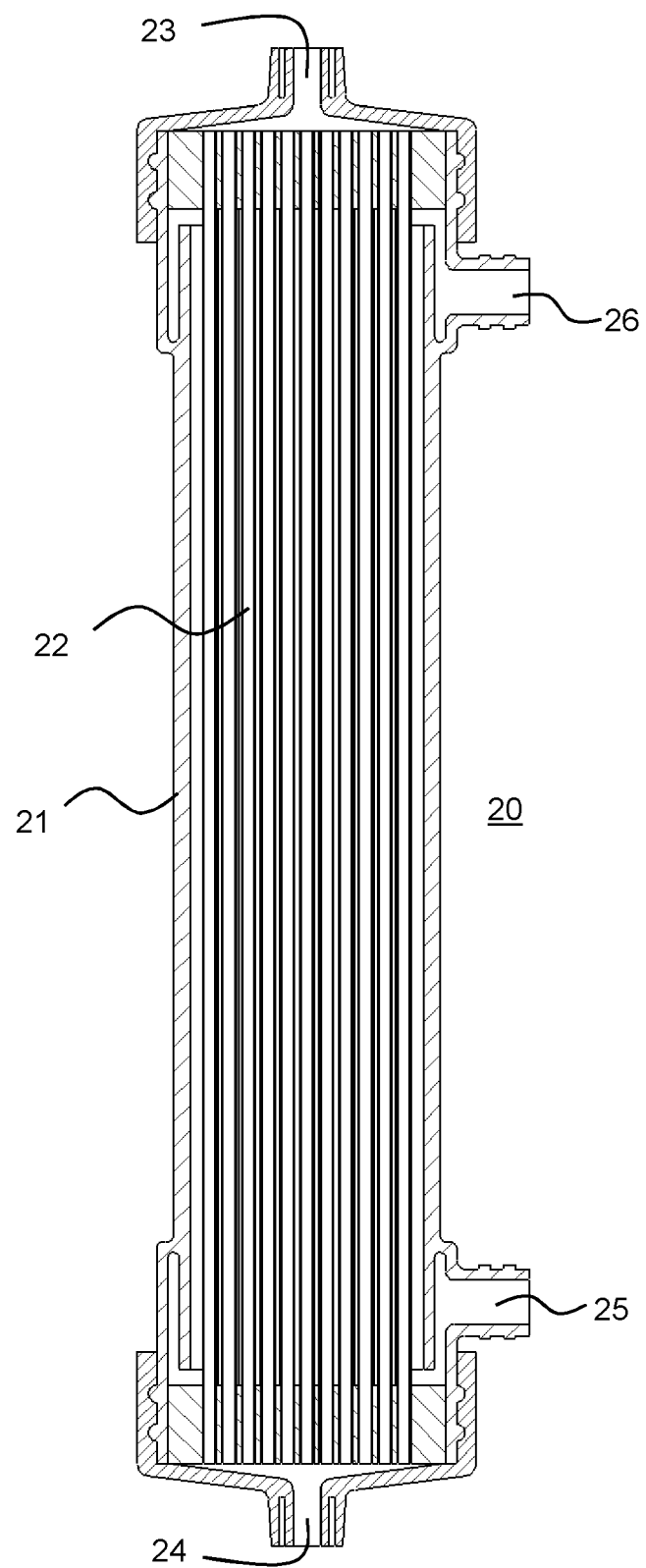
FIG. 10 is a cross-sectional view of a hemodialyzer.

As shown in FIG. 10, the hemodialyzer 20 includes a hemodialyzer container 21 having an internal space and a hemodialysis membrane 22 accommodated in the internal space of the hemodialyzer container. The internal space of the hemodialyzer container may be divided into a blood flow region and a dialysate flow region by the hemodialysis membrane. The hemodialyzer container is provided with a blood inlet 23 disposed at one end thereof and a blood outlet 24 disposed at the other end thereof. Also, a dialysate inlet 25 and a dialysate outlet 26 may be provided at an upper portion and a lower portion of the outer surface of the hemodialyzer container. FIG. 10 illustrates a hollow-fiber type hemodialyzer including hollow-fiber membranes, but the hemodialysis membrane according to an embodiment of the present invention may be configured to have a different shape of membrane, e.g., a flat membrane.

In this case, the transmembrane pressure (TMP) may be defined as the difference between a mean value of the hydraulic blood pressure at the blood inlet and outlet 23 and 24 and a mean value of the hydraulic dialysate pressure at the dialysate inlet and outlet 25 and 26. The TMP may be calculated in a different way, such as in consideration to an osmotic pressure as well as the hydraulic pressures of dialysate and blood. Or, it may be calculated by using any one of the hydraulic pressures at the blood inlet and outlet and any one of the hydraulic pressures at the dialysate inlet and outlet.

Figure 11:
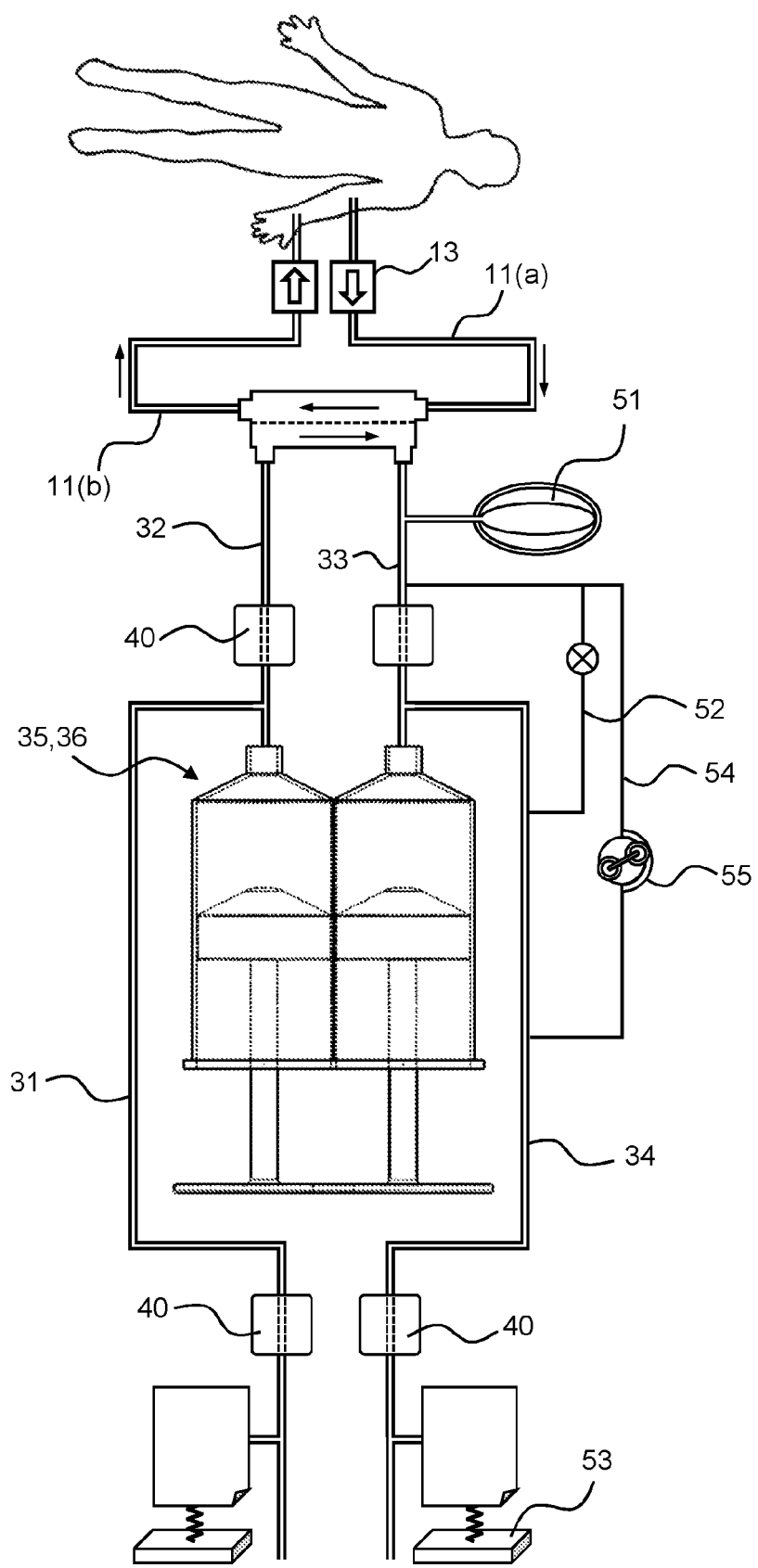
FIG. 11 is a schematic view illustrating a blood dialyzing apparatus having a one-way valve according to an embodiment of the present invention.

The blood dialyzing apparatus 10 according to an embodiment of the present invention is not limited to the structure shown in FIG. 9 and may be modified into another structure. FIG. 11 illustrates another exemplary blood dialyzing apparatus 10 in which the blood pump is replaced with a one-way valve 13 disposed on the blood tube to allow blood to flow in a predetermined direction. The blood tube 11 may include a first blood tube 11a to supply blood to the hemodialyzer and a second blood tube 11b to return blood of the hemodialyzer to a patient.

Figure 12A:
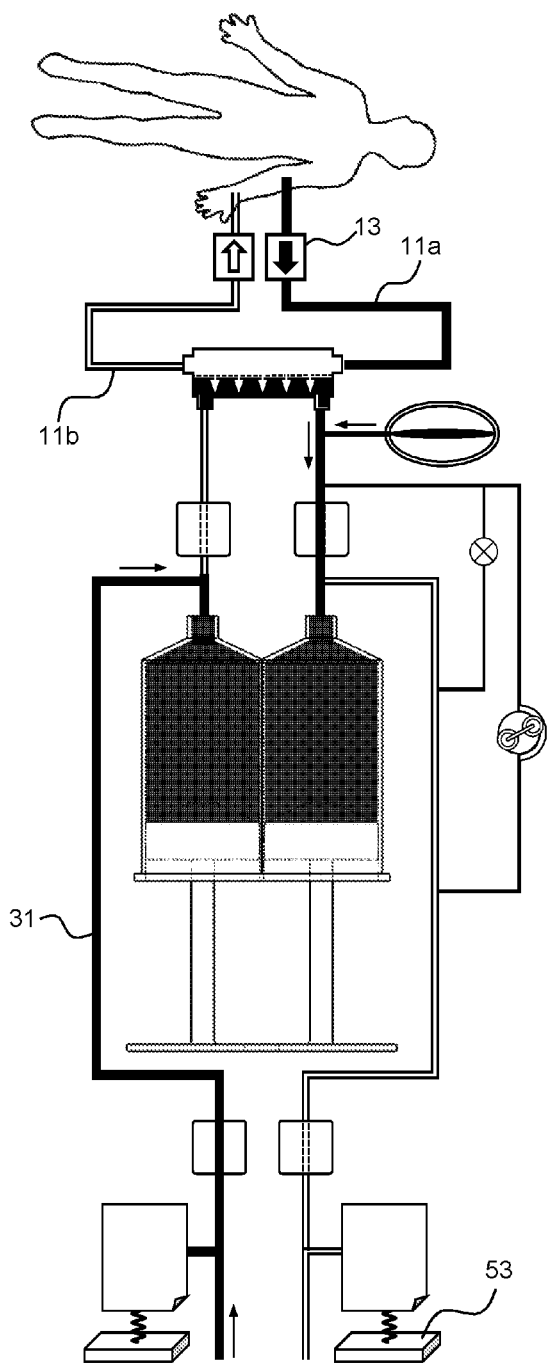
FIGS. 12A and 12B are views illustrating an operation of a blood dialyzing apparatus including a one-way valve according to an embodiment of the present invention.
Figure 12B:
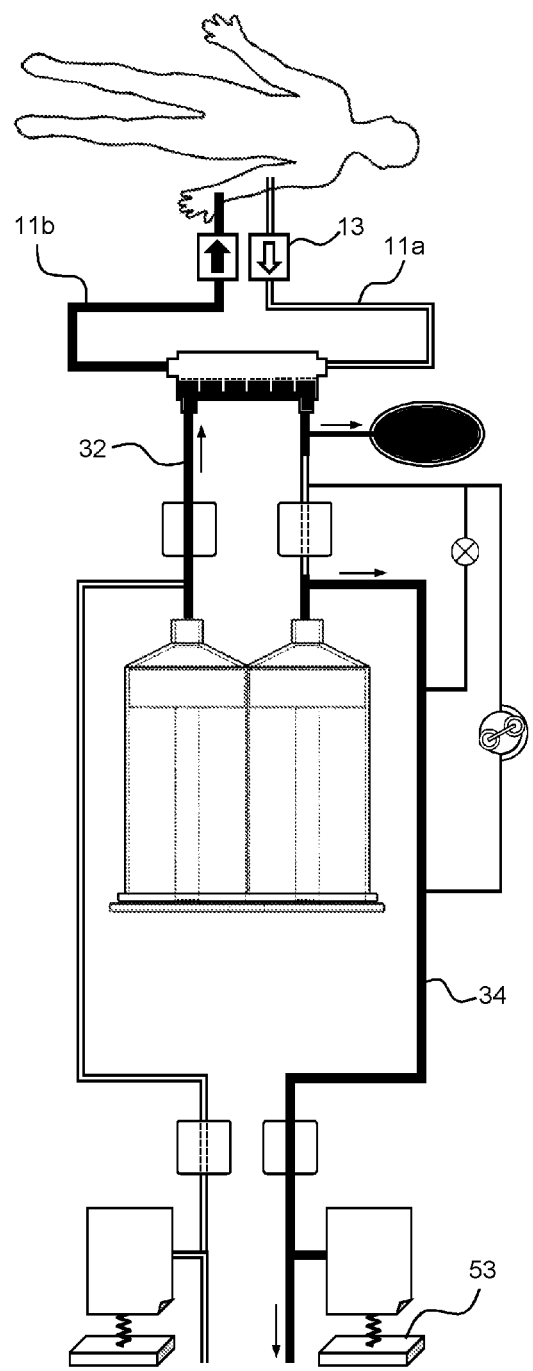

FIGS. 12A and 12B illustrate an operation of the blood dialyzing apparatus 10 having the one-way valve 13 and the dialysate supply device 30. The operation of the dialysate supply device 30 is illustrated in FIGS. 6A, 6B, 7A and 7B. As shown in FIG. 12A, when the cylinder 35a of the supply pump and the cylinder 36a of the recovery pump are expanded, the dialysate pressure of the hemodialyzer is lowered compared to the blood pressure and filtration in which water and waste products in blood move to the dialysate flow region occurs. Due to the filtration, blood of a patient is supplied to the hemodialyzer through the first blood tube 11a, resulting from the one-way valve 13 disposed on the blood tube. On the contrary, as shown in FIG. 12B, when the cylinders are compressed, the dialysate pressure of the hemodialyzer increases compared to the blood pressure, and backfiltration in which water in dialysate moves toward the blood flow region occurs. Due to the backfiltration, blood of the hemodialyzer is returned to a patient through the second blood tube 11b by the one-way valve 13 disposed on the blood tube.

Similarly, in the case of the blood dialyzing apparatus 10 in which the dialysate supply device 30 comprises the sac and sac pressurizing member or the roller and reservoir, blood may be supplied or returned to a patient through the blood tubes 11a and 11b during filtration and backfiltration, respectively, in substantially the same way as that shown in FIGS. 12A and 12B.

Accordingly, the dialysate supply device 30 according to an embodiment of the present invention can quickly change the dialysate pressure inside the hemodialyzer using the flow controller 40 opening or blocking dialysate flow and the supply and recovery pumps 35 and 36 which comprise the cylinder 35a and 36a and the piston 35b and 36b, the sac 35c and 36c and the sac pressurizing member 35d and 36d, or the roller 35e and 36e and the reservoir 35f and 36f. As a result, water exchange and mass transfer between blood and dialysate inside the hemodialyzer can be increased, thereby improving hemodialysis efficiency without increasing the size of the hemodialyzer or the flow rate of blood and dialysate. In addition, the blood dialyzing apparatus 10 according to an embodiment of the present invention transfers blood without using a blood pump, thereby allowing the blood dialyzing apparatus to be further miniaturized and lightened to thus provide a portable blood dialyzing apparatus.

The embodiment of the present invention described above and illustrated in the drawings should not be construed as limiting the technical spirit of the present invention. The scope of the present invention should be defined as disclosed in the accompanying claims, and those skilled in the art will appreciate that various modifications, additions and substitutions are possible without departing from the scope and spirit of the invention.

What is claimed is:

1. A dialysate supply device supplying and discharging dialysate, the dialysate supply device comprising:
   a supply pump supplying dialysate to a hemodialyzer;
   a recovery pump discharging dialysate of the hemodialyzer;
   a flow controller controlling a dialysate flow through a first dialysate tube connected to the supply pump through which dialysate is supplied to the supply pump, a second dialysate tube connecting the supply pump and the hemodialyzer through which dialysate of the supply pump is supplied to the hemodialyzer, a third dialysate tube connecting the hemodialyzer and the recovery pump through which dialysate of the hemodialyzer is discharged to the recovery pump, and a fourth dialysate tube connected to the recovery pump through which dialysate of the recovery pump is discharged; and
   a volume chamber connected to any one of the third dialysate tube or the second dialysate tube to store dialysate,
   wherein the supply pump and the recovery pump each comprise:
   a cylinder-shaped chamber having an internal space;
   a piston reciprocally disposed inside the cylinder-shaped chamber; and
   a piston driver driving the piston,
   wherein the cylinder-shaped chambers of the supply pump and the recovery pump are simultaneously compressed or simultaneously expanded.

2. The dialysate supply device of claim 1, further comprising a balance or a flowmeter to measure an amount of dialysate supplied to the hemodialyzer and an amount of dialysate collected from the hemodialyzer.

3. The dialysate supply device of claim 2, comprising a pressure-relief bypass connecting between the third dialysate tube and the fourth dialysate tube, or connecting between the second dialysate tube and the first dialysate tube.

4. A dialysate supply device comprising:
   a supply pump supplying dialysate to a hemodialyzer;

a recovery pump discharging dialysate of the hemodialyzer;

a flow controller controlling a dialysate flow through a first dialysate tube connected to the supply pump through which dialysate is supplied to the supply pump, a second dialysate tube connecting the supply pump and the hemodialyzer through which dialysate of the supply pump is supplied to the hemodialyzer, a third dialysate tube connecting the hemodialyzer and the recovery pump through which dialysate of the hemodialyzer is discharged to the recovery pump, and a fourth dialysate tube connected to the recovery pump through which dialysate of the recovery pump is discharged; and a volume chamber connected to any one of the third dialysate tube or the second dialysate tube to store dialysate, wherein the supply pump and the recovery pump each comprise:

a sac formed of a flexible material that contracts and relaxes;

a sac pressurizing member compressing the sac to discharge dialysate out of the sac; and a sac pressurizing member driver providing a reciprocating movement force to the sac pressurizing member, wherein the sac of the supply pump and the sac of the recovery pump are repeated to be simultaneously compressed or simultaneously expanded.

5. The dialysate supply device of claim 4, further comprising a balance or a flowmeter to measure an amount of dialysate supplied to the hemodialyzer and an amount of dialysate collected from the hemodialyzer.

6. The dialysate supply device of claim 5, comprising a pressure-relief bypass connecting between the third dialysate tube and the fourth dialysate tube, or connecting between the second dialysate tube and the first dialysate tube.

7. A dialysate supply device comprising:

a supply pump supplying dialysate to a hemodialyzer;

a recovery pump discharging dialysate of the hemodialyzer;

a flow controller controlling a dialysate flow through a first dialysate tube connected to the supply pump through which dialysate is supplied to the supply pump, a second dialysate tube connecting the supply pump and the hemodialyzer through which dialysate of the supply pump is supplied to the hemodialyzer, a third dialysate tube connecting the hemodialyzer and the recovery pump through which dialysate of the hemodialyzer is discharged to the recovery pump, and a fourth dialysate tube connected to the recovery pump through which dialysate of the recovery pump is discharged; and a volume chamber connected to any one of the third dialysate tube or the second dialysate tube to store dialysate, wherein the supply pump and the recovery pump each comprise:

a reservoir storing dialysate;

a roller transferring dialysate by compressing the dialysate tube; and a roller driver driving the roller, wherein the roller of the supply pump and the roller of the recovery pump rotate in a same direction.

8. The dialysate supply device of claim 7, further comprising a balance or a flowmeter to measure an amount of dialysate supplied to the hemodialyzer and an amount of dialysate collected from the hemodialyzer.

9. The dialysate supply device of claim 8, comprising a pressure-relief bypass connecting between the third dialysate tube and the fourth dialysate tube, or connecting between the second dialysate tube and the first dialysate tube.

10. The dialysate supply device of claim 3, wherein the pressure-relief bypass is opened or closed by at least one of a difference of pressures inside tubes to which opposite ends of the pressure-relief bypass are connected, a pressure of the third dialysate tube, a pressure of the second dialysate tube, or a TMP of the hemodialyzer.

11. The dialysate supply device of claim 1, wherein the flow controller comprises:

a flow-blocking member;

a support wall supporting at least one of the dialysate tubes compressed by the flow-blocking member; and a flow-blocking member driver driving the flow-blocking member.

12. The dialysate supply device of claim 1, wherein the flow controller comprises:

a housing;

a flow port disposed on an outer surface of the housing;

a rotor disposed inside the housing to connect a flow passage between the flow ports; and a rotor driver driving the rotor.

13. The dialysate supply device of claim 12, wherein a flow path is disposed inside the rotor.

14. The dialysate supply device of claim 13, wherein the flow path has a fan shape extending outwardly from a middle portion of the rotor.

15. The dialysate supply device of claim 1, further comprising:

an auxiliary effluent outflow tube connecting between the third dialysate tube and the fourth dialysate tube; and an auxiliary effluent pump disposed on the auxiliary effluent outflow tube to pull dialysate of the hemodialyzer.

16. The dialysate supply device of claim 1, further comprising a flowmeter to measure an amount of dialysate supplied to the hemodialyzer and an amount of dialysate collected from the hemodialyzer.

* * * * *